United States Patent [19]
Ao et al.

[11] Patent Number: 5,179,203
[45] Date of Patent: Jan. 12, 1993

[54] THIADIAZINE COMPOUND WITH A NOVEL CRYSTALLINE FORM

[75] Inventors: Hideki Ao, Oita; Shinro Setoguchi, Fukuoka; Yasuhiko Ishida, Oita, all of Japan

[73] Assignee: Yoshitomi Pharmaceutical Industries Ltd., Osaka, Japan

[21] Appl. No.: 560,634

[22] Filed: Jul. 31, 1990

[51] Int. Cl.$^5$ .......................... C07D 417/04
[52] U.S. Cl. ...................... 544/8; 544/238; 544/239
[58] Field of Search ............ 544/8, 238, 239; 514/222.5

[56] References Cited

U.S. PATENT DOCUMENTS 4,678,785  7/1987  Ao et al. ............ 514/222.5

FOREIGN PATENT DOCUMENTS 0180158  5/1986  European Pat. Off. ......... 514/222.5

OTHER PUBLICATIONS

European Search Report.
Fortschritte der Arzneimittelforschung, vol. 10, 1966, Basel, CH; K. Munzel: "Der Einfluss der Formgebung auf die Wirkung eines Arzneimittels", pp. 227–230.
Pharmaceutics of Solids and Solid Dosage Forms by Jens T. Carstensen, 1977, pp. 5–8.
The International Pharmacopoeia, 3rd Edition, vol. 1, General Methods of Analysis, 1979, pp. 19–23.
USP XXII NF XVII The United States Pharmacopeia—The National Formulary, Jan. 1, 1990, pp. 1588–1589.
USP XXII NF XVII The United States Pharmacopeia—The National Formulary, Jan. 1, 1990, pp. 98, 945, 310, 685.

Primary Examiner—Mukund J. Shah
Assistant Examiner—Y. N. Gupta
Attorney, Agent, or Firm—Sughrue Mion Zinn Macpeak & Seas

[57] ABSTRACT

Novel β-form crystals of 6-(3,6-dihydro-2-oxo-2H-1,3,4-thiadiazin-5-yl)-3,4-dihydro-2(1H)-quinolinone useful as cardiotonics.

2 Claims, 3 Drawing Sheets

THIADIAZINE COMPOUND WITH A NOVEL CRYSTALLINE FORM

BACKGROUND OF THE INVENTION

The present invention relates to pharmaceutically useful 6-(3,6-dihydro-2-oxo-2H-1,3,4-thiadiazin-5-yl)-3,4-dihydro-2(1H)-quinolinone with a novel crystalline form.

The U.S. Pat. No. 4,678,785 discloses that 5-3,4-dihydrocarbostyril-6-yl)-3,6-dihydro-1,3,4-thiadiazin-2-one [another nomenclature : 6-(3,6-dihydro-2-oxo-2H-1,3,4-thiadiazin-5-yl)-3,4-dihydro-2(1H)-quinolinone, hereinafter referred to as compound(I)]which is useful as cardiotonics, is obtained by reacting 6-chloroacetyl-3,4-dihydro-2(1H)-quinolinone with ethoxythiocarbonylhydrazine in acetonitrile followed by recrystallizing the resulting crystals from a mixture of dimethylformamide and water. However, the thus obtained crystals (hereinafter referred to as α-form crystals of the compound (I)) are pale yellow cotton-like powders with low bulk density, tend to be electrified with static charge and are difficult to handle. The charged particles used to repel one another and easily diffuse into air. Furthermore., the α-form crystals of the compound (I) are unstable to be easily changed into different crystal form by the physical force. These properties are not satisfactory in precise measurability and workability during various handlings, especially in preparing pharmaceutical formulations.

The present inventors have made intensive investigations in order to solve the such problems and provide a novel crystal of the compound (I) which is suitable for preparing the pharmaceutical formulations. As a result, the inventors have found that the α-form crystals obtained by the method of aforesaid publication are heated, grinded or rubbed to give stable crystals of the compound (I) with good quality and convenience in handlings. These findings have resulted in the accomplishment of this invention.

SUMMARY OF THE INVENTION

The present invention relates to 6-(3,6-dihydro-2-oxo-2H-1,3,4-thiadiazin-5-yl)-3,4-dihydro-2(1H)-quinolinone with a novel crystalline form [hereinafter referred to as β-form crystals of the compound (I)) showing sharp X-ray diffraction peaks at the diffraction angle $2\theta = 19.5°$, 23.0° and 29.0° when measured with X-ray of Cu-Kα wavelength and having bulk density of 50-65 g/100 cc. The β-form crystals of the present invention are characterized by higher bulk density, the absence of dispersion thereof into air and better fluidity.

(Magnification of each photograph is ×500.)

DETAILED DESCRIPTION

According to this invention, the novel β-form crystals of the compound (I) can be obtained by, for example, heating the α-form crystals of the compound (I). That is to say, the compound (I) with a novel crystalline form (β-form crystals) can be prepared by heating the suspension of α-form crystals in water or a mixture of water and a water-soluble solvent under reflux with stirring for 30 minutes to 10 hours and subsequently removing the solvent. The water-soluble solvent means water-soluble alcohol such as $C_{1-4}$ alkanol or $C_{2-4}$ alkanediol, water-soluble ketone, water-soluble ether, water-soluble $C_{1-4}$ alkanoic acid, and includes, for example, methanol, ethanol, propanol, isopropyl alcohol, tertiary butyl alcohol, ethylene glycol, propylene glycol, 1,3-butanediol, acetone, methyl ethyl ketone, dioxane, tetrahydrofuran, formic acid, acetic acid, propionic acid, n-butyric acid and so on. Water per se can be used as the solvent, but the α-form crystals of the compound (I) tend to float on water, so that a mixed solvent of water and the above-mentioned water-soluble solvent is preferably usable. In the present invention, the amount of water and the water-soluble solvent may be ranged at a volume proportion of 1:0 to 1:10 and preferably at 1:1 to 1:5. The heating temperature is preferably in the range from 40° C. to 100° C.

Figure 1:
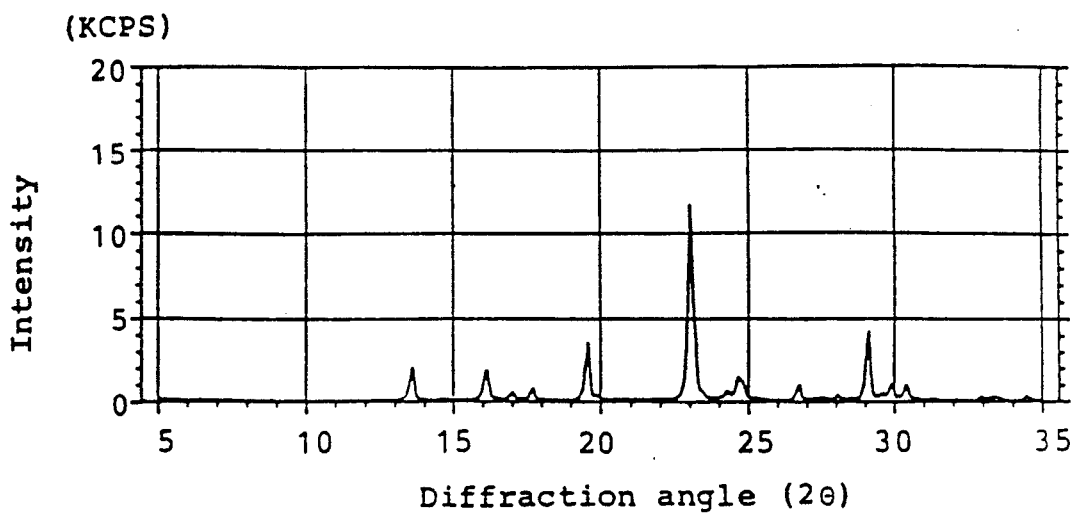
FIG. 1 shows X-ray diffraction pattern of β-form crystals of the compound (I)

The β-form crystals obtained according to this invention have a diffraction pattern measured with a X-ray apparatus (Cu-Kα, graphite monochromator, 50 KV, 30 mA), namely, X-ray diffraction intensity with the diffraction angle $2\theta$ as shown in Table 1 and an X-ray diffraction pattern as shown in FIG. 1.

TABLE 1

| No. | Diffraction angle 2θ (°) | d(A) | Relative intensity $I/I_1$ (%) |
|---|---|---|---|
| 1 | 29.050 | 3.0712 | 36 |
| 2 | 24.628 | 3.6117 | 12 |
| 3 | 23.008 | 3.8622 | 100 |
| 4 | 19.549 | 4.5369 | 28 |
| 5 | 16.091 | 5.5035 | 11 |
| 6 | 13.552 | 6.5285 | 12 |

Specifically, the sharp X-ray diffraction peaks at the diffraction angle $2\theta = 19.5°$, 23.0° and 29.0° enables to identify the novel β-form crystals of 6-(3,6-dihydro-2-oxo-2H-1,3,4-thiadiazin-5-yl)-3,4-dihydro-2(1H)-quinolinone (Compound (I)) and distinguish said novel crystalline structure from the α-form crystals. The β-form crystals of the compound (I) are slightly yellowish white crystals and are also characteristic on the point that the melting point thereof is 276°-280° C. (with decomposition), somewhat higher than the α-form crystals as described below.

Figure 3:
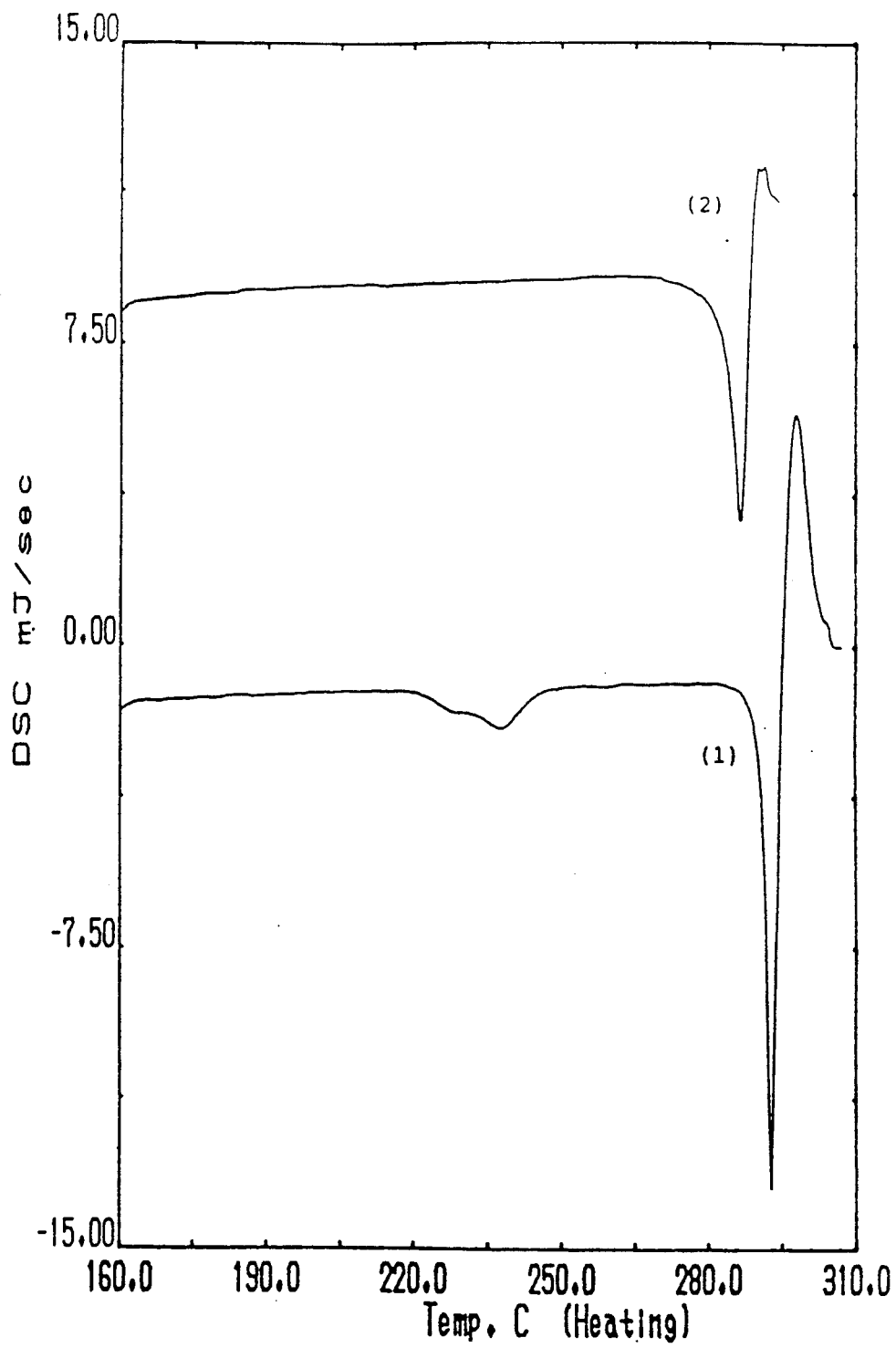
FIG. 3 shows a chart of differential scanning calorimetry of β-form and α-form crystals of the compound (I)

Furthermore, the bulk density of β-form crystals of the compound (I) is about 50 to about 65 g/100 cc. The differential scanning calorimetry measured by differential scanning calorimeter (DSC-20, Seiko Electronic K.K.) shows the curve (1) in the FIG. 3 (measurement condition: Sample weight 2mg, Heating rate 10 deg/min.), and a wide endothermic peak around at 230° C. and a decomposition peak around at 295° C. can be observed.

Figure 2:
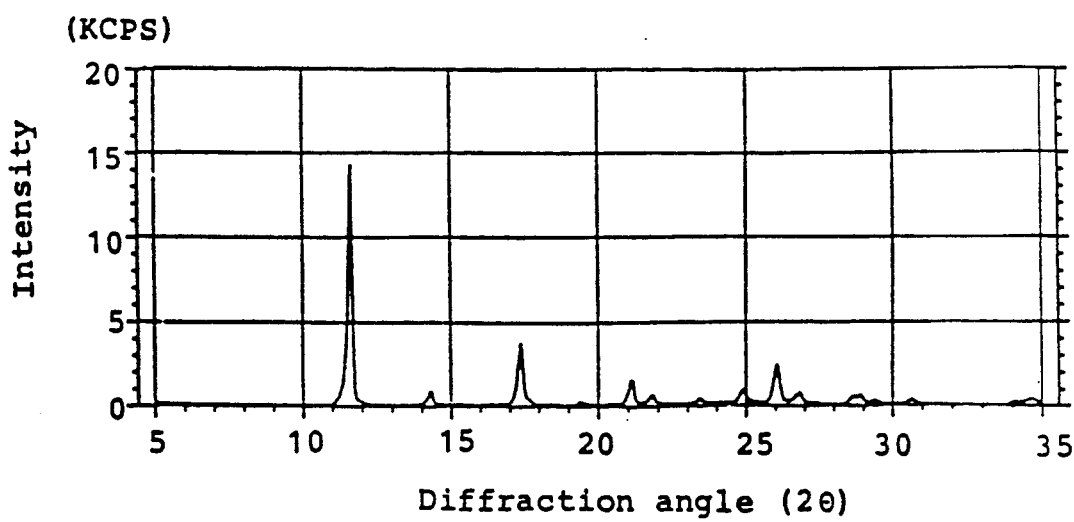
FIG. 2 shows X-ray diffraction pattern of α-form crystals of the compound (I)

On the other hand, α-form crystals of the compound (I) have the following X-ray diffraction pattern measured at the same condition as above, namely, X-ray diffraction intensity with the diffraction angle 28 as shown in Table 2 and X-ray diffraction pattern as shown in FIG. 2.

TABLE 2

| No. | Diffraction angle | | Relative intensity |
|---|---|---|---|
| | $2\theta$ (°) | d(A) | $I/I_1$ (%) |
| 1 | 26.029 | 3.4204 | 23 |
| 2 | 21.082 | 4.2105 | 14 |
| 3 | 17.360 | 5.1037 | 27 |
| 4 | 11.581 | 7.6342 | 100 |

Specifically, the α-form crystals show sharp diffraction peaks at the diffraction angle $2\theta$ 32 11.5° and 17.3° and the melting point thereof is 271°-272° C. (decomposition).

The bulk density of α-form crystals is about 25 to 35 g/100 cc. The differential scanning calorimetry was measured under the same condition to show the pattern (2) in the FIG. 3 having a decomposition peak around at 285° C.

Figure 4:
FIG. 4 shows an electron microscopic photograph of β-form crystals of the compound (I)
Figure 5:
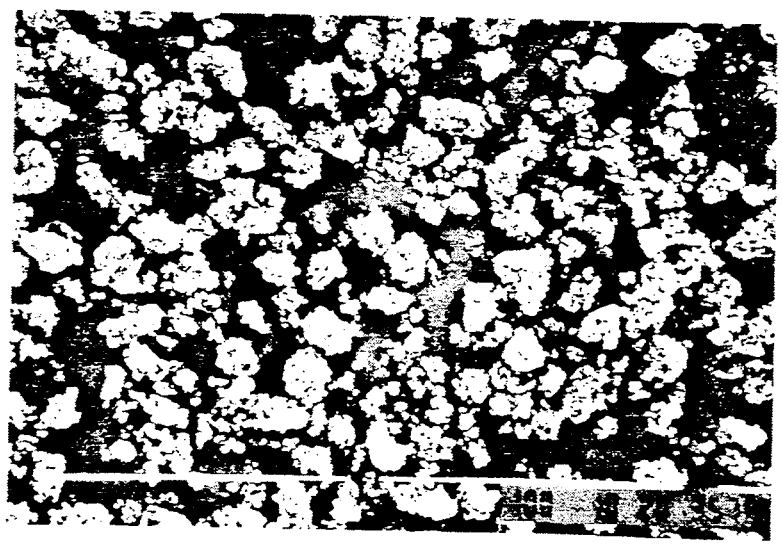
FIG. 5 shows an electron microscopic photograph of α-form crystals of the compound (I).

Furthermore, the external appearance of the β-form crystals of the compound I) is quite different from that of α-form crystals as shown in FIG. 4 and FIG. 5.

The β-form crystals of compound (I) obtained in accordance with the present invention, unlike the hitherto known crystals in the α-form, is characterized by higher bulk density, absense of dispersion thereof into air and good fluidity. Besides, the β-form crystals are stable ones because they are no longer altered into other crystal forms by any force.

These characteristic properties have improved transportability, measurability (no fluctuation of weight in preparing the pharmaceutical formulations) and workability (easiness to crush the crystals and to kneed it with a binder, or no danger caused by the charged particles during the kneading and drying operations), so that it is covenient to make the pharmaceutical formulations such as tablets, granules, capsules or the like. Since the cardiotonic activity of the β-form crystals is almost the same as that of α-form crystals, β-form crystals are useful as cardiotonics.

Below, the present invention is specifically described by examples.

REFERENCE EXAMPLE

To a solution of acetonitrile (100 ml) were added 6-chloro-acetyl-3,4-dihydro-2(1H)-quinolinone (6.7 g) and ethoxythiocarbonylhydrazine (5.4 g) and the mixture was stirred for 2 hours, cooled and then filtered off. The filtrate was recrystallized from dimethylformamide (30 ml) and water (10 ml) to obtain pale yellow 6-(3,6-dihydro-2-oxo-2H-1,3,4-thiadiazin-5-yl)-3,4-dihydro-2(1H)-quinolinone (5.2 g), melting at 271°-272° C. (decomposition).

The X-ray diffraction of the crystals were measured to obtain the pattern of α-form crystals as shown in the FIG. 2.

EXAMPLE 1

α-Form crystals of 6-[3,6-dihydro-2-oxo-2H-1,3,4-thiadiazin-5-yl)-3,4-dihydro-2(1H)-quinolinone (10g) were suspended in a mixture of ethanol (100 ml) and water (100 ml). The suspension was refluxed under heating with stirring for three hours. The resulting crystals were collected by filtration and dried to give slightly yellowish white crystals of compound (I), melting at 276°-280° C. with decomposition.

The melting point and the X-ray diffraction pattern as shown in FIG. 1 confirmed that these crystals were in the β-form.

The β-form crystals of compound (I) can be safely administered as cardiotonics, in the form of a pharmaceutical preparation with a suitable and conventional pharmaceutically acceptable carrier, without adversely affecting the patients.

The pharmaceutical formulations can take any conventional form such as tablets, capsules, granules, powder or injectable solutions.

The followings are examples of formulations when a compound (I) of this invention is administered for pharmaceutical purposes:

(1) Tablets

A composition of 1 part of the β-form crystals of compound (I), 25 parts of lactose, 35 parts of crystalline cellulose and 3 parts of corn starch is mixed well, and kneaded with binder prepared by 2 parts of corn starch. The paste is passed through a 16 mesh sieve and dried in an oven at 50° C., and forced through a 24 mesh sieve. The powder thus obtained, 8 parts of corn starch, 11 parts of crystalline cellulose and 9 parts of talc are mixed well and the mixture was compressed with a punch into tablets containing 1 mg of active ingredient.

(2) 1% Powder

A composition of 1 part of the β-form crystals of compound (I) and 90 parts of lactose is mixed well and kneaded with binder prepared by a suitable amount of methylcellulose. The mixture was passed through a 16 mesh sieve and dried in an oven at 50° C. The dried granules were forced through 32 mesh sieve with pressure and mixed with a suitable amount of silicon dioxide to produce 1% powder

What is claimed is:

1. 6-(3,6-Dihydro-2-oxo-2H-1,3,4-thiadiazin-5-yl)-3,4-dihydro-2(1H)-quinolinone with a β-crystalline form showing sharp X-ray diffraction peaks at the diffraction angle $2\theta = 19.5°$, 23.0° and 29.0° when measured with X-ray of Cu-Kα wavelength.

2. 6-(3,6-Dihydro-2-oxo-2H-1,3,4-thiadiazin-5-yl)-3,4-dihydro-2(1H)-quinolinone of claim 1 of which bulk density is 50-65 g/100 cc.

* * * * *